Sept. 3, 1957 E. S. BOERNER Plant Pat. 1,638
CHRYSANTHEMUM PLANT
Filed Dec. 5, 1956
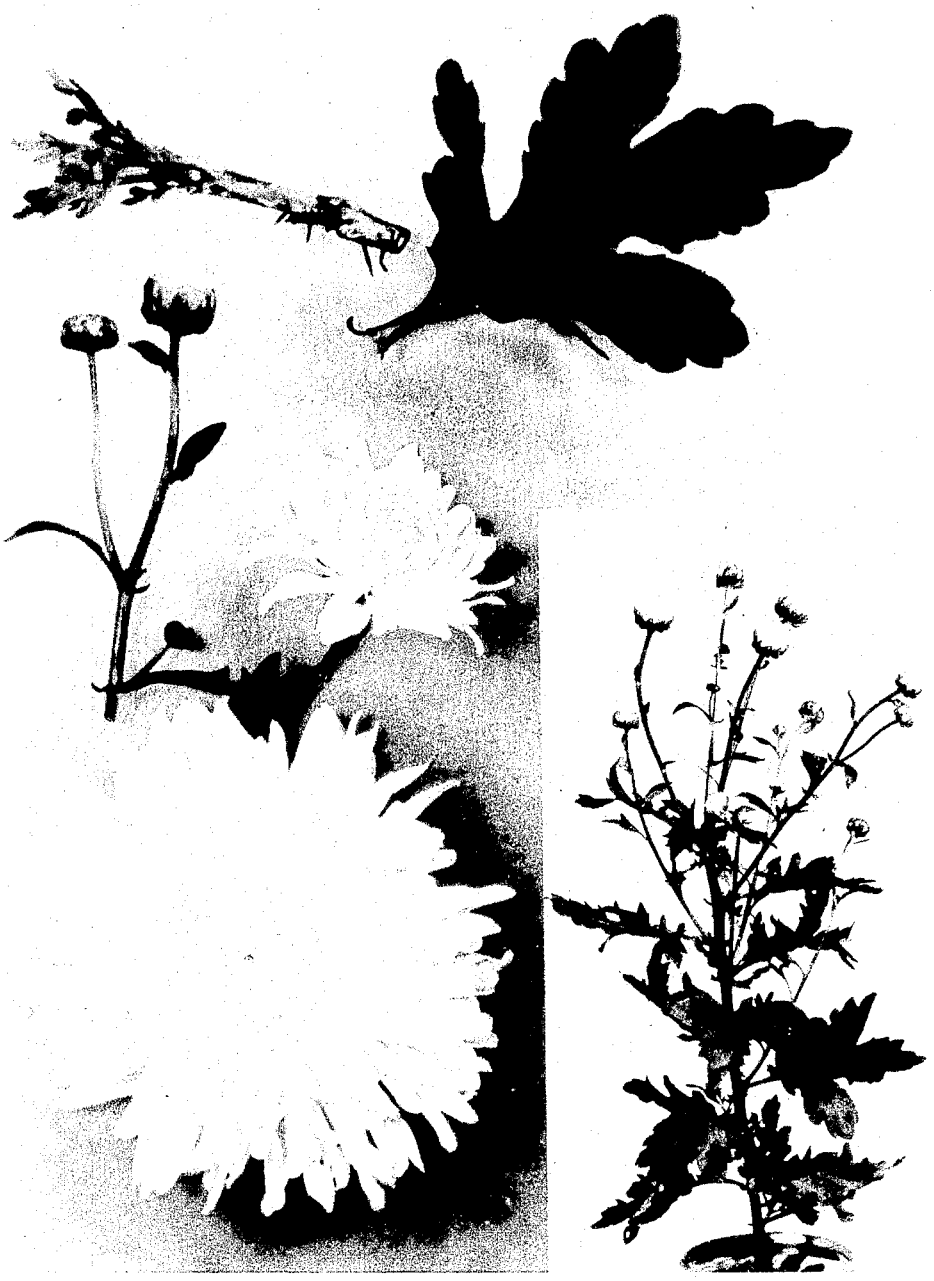
Inventor.
E. S. Boerner
By: Robert Cobb
Attorneys United States Patent Office Plant Pat. 1,638
Patented Sept. 3, 1957

1,638

CHRYSANTHEMUM PLANT

Eugene S. Boerner, Newark, N. Y., assignor to Jackson & Perkins Company, Newark, N. Y., a corporation of New York Application December 5, 1956, Serial No. 626,565

1 Claim. (Cl. 47—60)

The present invention relates to a new and distinct variety of chrysanthemum plant which was discovered by me as a cultivated sport of the chrysanthemum variety named "Cockatoo" (Plant Patent No. 1,171), growing in a field of plants under my supervision and control on property owned by the assignee hereof, at Newark, New York.

My attention was initially directed to the sport by the distinctly different color of the blooms thereof, which are characterized as Picric Yellow, lightly overcast with Empire Yellow, in general color tonality, as distinguished from the usual Martius Yellow color of the center of the flowers of the parent variety and the Sea-Foam Yellow color of the outer petals of the latter variety. The aforesaid color of the blooms of the sport is new in the chrysanthemum world, and differs from the color of any other chrysanthemum variety of which I am aware.

Continued observations of the sport, and asexual reproduction thereof, as performed by me by top cuttings and also by underground runners, at Newark, New York, have shown and definitely demonstrated that the color characteristics of my new variety come true to form and are established and transmitted through succeeding propagations. Except for the distinctive color of the blooms, the new variety is otherwise substantially identical to the parent variety "Cockatoo."

The accompanying drawing shows typical specimens of the foliage, stems and flowers of my new variety in different stages of development and as depicted in color as nearly true as it is reasonably possible to make the same in a color illustration of this character, as well as a specimen plant depicted in black-and-white which is illustrative of the typical habit of growth of the plant.

The following is a detailed description of my new variety, with color terminology in accordance with Ridgway's Color Standards and Nomenclature, as based upon observations of specimens grown outdoors at Newark, New York, in the early morning during the latter part of September.

Parentage: Sport of "Cockatoo."

Classification: Semi-decorative type; petals finish uneven, giving flowers an attractive ragged appearance.

Growth: Bushy; tall; attains height of three feet.

Cold Resistance: Plant is very winter-hardy in northern New York; flowers are frost-resistant.

Blooming Period: In the Newark, New York, climatic area, blooming begins about September 15th and continues until severe freezing temperatures.

Bud:

*Color.*—When sepals first divide—Light Chalcedony Yellow, Plate 17. When petals begin to unfurl—Pale Lemon Yellow, Plate 4. When half-blown: inside—Lemon Yellow, Plate 4; outside—Empire Yellow, Plate 4, lightly overcast with Lemon Yellow, Plate 4.

*Peduncle.*—Strong. Color—Kildare Green, Plate 31.

Bloom:

*Size.*—From 4 to 4½ inches.

*Stem.*—Strong; normal.

*Form.*—Semi-decorative.

*Petalage.*—Double.

*Color.*—Center of flower—Empire Yellow, Plate 4. Outer petals—Picric Yellow, Plate 4. Base of petals—Pal Greenish Yellow, Plate 5. Inside of petals—Picric Yellow, Plate 4, lightly overcast with Empire Yellow, Plate 4. Reverse of petals—Martius Yellow, Plate 4.

*Petals.*—Texture—Thick. Form—Long; petals finish unevenly, giving an attractive ragged appearance.

*Fragrance.*—Characteristic chrysanthemum.

*Plant*

Form: Upright.

Growth: Vigorous; free; full.

Foliage:

*Size.*—Normal.

*Quantity.*—Normal.

*Color.*—Upper side—Dark Dull Yellow-Green, Plate 32. Reverse side—Bice Green, Plate 17.

*Texture.*—Leathery.

I claim:

A new and distinct variety of chrysanthemum plant of the semi-decorative type, substantially as herein shown and described, characterized particularly as to novelty by being substantially identical with the chrysanthemum variety "Cockatoo" (Plant Patent No. 1,171), except for the new and distinctive Picric Yellow, lightly overcast with Empire Yellow, general color tonality of its blooms.

No references cited.